United States Patent
Onda et al.

(10) Patent No.: US 11,644,449 B2
(45) Date of Patent: May 9, 2023

(54) SENSING SYSTEM, INFORMATION PROCESSING APPARATUS, AND SENSOR APPARATUS

(71) Applicant: TAIYO YUDEN CO., LTD., Tokyo (JP)

(72) Inventors: Yosuke Onda, Gunma (JP); Masashi Hattori, Gunma (JP); Kenichi Shimomai, Gunma (JP); Jin Mikata, Gunma (JP); Taiji Ito, Gunma (JP)

(73) Assignee: TAIYO YUDEN CO., LTD., Tokyo (JP)

(*) Notice: Subject to any disclaimer, the term of this patent is extended or adjusted under 35 U.S.C. 154(b) by 247 days.

(21) Appl. No.: 16/957,039

(22) PCT Filed: Nov. 5, 2018

(86) PCT No.: PCT/JP2018/041066
§ 371 (c)(1),
(2) Date: Jun. 22, 2020

(87) PCT Pub. No.: WO2019/123864
PCT Pub. Date: Jun. 27, 2019

(65) Prior Publication Data
US 2020/0393430 A1      Dec. 17, 2020

(30) Foreign Application Priority Data

Dec. 22, 2017  (JP) ............... JP2017-247051

(51) Int. Cl.
*G01N 33/00*      (2006.01)
*G01N 29/02*      (2006.01)

(52) U.S. Cl.
CPC ....... *G01N 33/0001* (2013.01); *G01N 29/022* (2013.01)

(58) Field of Classification Search
CPC .......... G01N 33/0031; G01N 33/0047; G01N 33/0001; G01N 33/497; G01N 21/3504; G01N 1/2273
See application file for complete search history.

(56) References Cited

U.S. PATENT DOCUMENTS

| 5,675,070 A | * | 10/1997 | Gelperin | ............ G01N 33/0031 73/23.34 |
| 6,672,129 B1 | * | 1/2004 | Frederickson | ...... A61M 15/025 73/1.06 |

(Continued)

FOREIGN PATENT DOCUMENTS

| CN | 1439876 A | 9/2003 |
| CN | 103649738 A | 3/2014 |

(Continued)

OTHER PUBLICATIONS

Eungyeong Kim et al., "Pattern Recognition for Selective Odor Detection with Gas Sensor Arrays", Sensors, vol. 12, Nov. 23, 2012. (Year: 2012).*

(Continued)

*Primary Examiner* — David A. Rogers
(74) *Attorney, Agent, or Firm* — Chen Yoshimura LLP

(57) ABSTRACT

An odor is detected with high accuracy. A sensing system includes: a sensor apparatus including a filter to remove an odor-causing substance contained in air and a sensor unit including one or more detection elements to detect an amount of the odor-causing substance contained in air; and an information processing apparatus including a difference calculation unit to calculate a difference between a detection value of each of the one or more detection elements, the detection value indicating an amount of the odor-causing substance contained in air that has passed through the filter and a detection value of each of the one or more detection elements, the detection value indicating an amount of the (Continued)

odor-causing substance contained in air that has not passed through the filter, and a determination unit to determine an odor of air based on the calculated difference.

6 Claims, 9 Drawing Sheets

(56) References Cited

U.S. PATENT DOCUMENTS

| | | | |
|---|---|---|---|
| 6,759,010 B2 * | 7/2004 | Lewis | G01N 15/0826 73/23.3 |
| 8,083,575 B2 * | 12/2011 | Kim | B60H 1/00285 297/180.14 |
| 8,880,448 B2 * | 11/2014 | Haddad | G01N 33/0073 512/1 |
| 9,125,590 B2 * | 9/2015 | Tang | G01N 33/497 |
| 9,377,447 B2 * | 6/2016 | Mershin | G01N 33/0031 |
| 9,470,654 B2 * | 10/2016 | Kubinski | G01N 27/417 |
| 9,704,095 B2 * | 7/2017 | Jacquot | G06N 3/08 |
| 10,049,324 B2 * | 8/2018 | Angell | G06N 5/04 |
| 10,386,350 B2 * | 8/2019 | Richter | G01N 33/0036 |
| 10,604,257 B2 * | 3/2020 | Hwang | A61L 9/14 |
| 10,710,429 B2 * | 7/2020 | MacNeille | B60H 3/06 |
| 10,839,440 B2 * | 11/2020 | Amin | G06F 16/9537 |
| 2002/0000115 A1 | 1/2002 | Nakano et al. | |
| 2003/0172717 A1 | 9/2003 | Kita et al. | |
| 2008/0188172 A1 | 8/2008 | Hollemans et al. | |
| 2010/0139366 A1 * | 6/2010 | Krausch | D06F 34/14 68/13 R |
| 2010/0241306 A1 | 9/2010 | Akisada et al. | |
| 2012/0150790 A1 * | 6/2012 | Angell | G06F 16/284 706/54 |
| 2013/0061692 A1 * | 3/2013 | Muresan | G01N 33/0031 73/863 |
| 2014/0099729 A1 * | 4/2014 | Mershin | G01N 33/0031 422/83 |
| 2014/0174154 A1 | 6/2014 | Marra et al. | |
| 2015/0268158 A1 * | 9/2015 | Laudo | G01N 33/0047 250/349 |
| 2016/0169851 A1 * | 6/2016 | Lee | G01N 33/0001 73/23.34 |
| 2016/0327501 A1 | 11/2016 | Vogel et al. | |
| 2017/0000277 A1 | 1/2017 | Johnson et al. | |
| 2017/0080374 A1 | 3/2017 | Fox et al. | |
| 2017/0199159 A1 | 7/2017 | Kuroki et al. | |
| 2018/0328767 A1 | 11/2018 | Adachi et al. | |
| 2019/0227053 A1 * | 7/2019 | Rinberg | G01N 33/5088 |
| 2020/0111189 A1 * | 4/2020 | Yeung | G06Q 10/02 |
| 2021/0188051 A1 * | 6/2021 | MacNeille | B60H 3/0085 |

FOREIGN PATENT DOCUMENTS

| | | | | |
|---|---|---|---|---|
| CN | 103913484 A | 7/2014 | | |
| CN | 104180855 A | 12/2014 | | |
| CN | 105241821 A | 1/2016 | | |
| CN | 106124750 A | 11/2016 | | |
| CN | 106662517 A | 5/2017 | | |
| CN | 106706863 A | 5/2017 | | |
| CN | 106950293 A | 7/2017 | | |
| EP | 1566633 A1 * | 8/2005 | ......... | G01N 33/0001 |
| JP | H05-312708 A | 11/1993 | | |
| JP | H11-15613 A | 6/1999 | | |
| JP | 2000-019137 A | 1/2000 | | |
| JP | 2000-210518 A | 8/2000 | | |
| JP | 3074494 U | 1/2001 | | |
| JP | 2002-022692 A | 1/2002 | | |
| JP | 2005-083960 A | 3/2005 | | |
| JP | 2005-147793 A | 6/2005 | | |
| JP | 2006-015907 A | 1/2006 | | |
| JP | 2008-032607 A | 2/2008 | | |
| JP | 2009-240976 A | 10/2009 | | |
| JP | 2011-145815 A | 7/2011 | | |
| JP | 2012-021849 A | 2/2012 | | |
| JP | 2014-518398 A | 7/2014 | | |
| JP | 2016-199098 A | 12/2016 | | |
| JP | 2017-161300 A | 9/2017 | | |
| WO | 2008/018283 A1 | 2/2008 | | |
| WO | 2016/052049 A1 | 4/2016 | | |

OTHER PUBLICATIONS

Hwi Jin Ko et al., "Bioelectronic nose and its application to smell visualization", Journal of Biological Engineering, 2016. (Year: 2016).*

Niranjan S. Ramgir, "Electronic Nose Based on Nanomaterials: Issues, Challenges, and Prospects", Hindawi Publishing Corporation, ISRN Nanomaterials, vol. 2013, Article ID 941581, 2013. (Year: 2013).*

Seth Haney et al., "Differential effects of adaptation on odor discrimination", Journal of Neurophysiology, No. 120, 2018. (Year: 2018).*

International Search Report (ISR) issued in PCT/JP2018/041066 dated Dec. 2018.

Written Opinion (PCT/ISA/237) issued in PCT/JP2018/041066 dated Dec. 2018. (Concise Explanation of Relevance: This Written Opinion considers that some of the claims are described by the references and U.S. Patent Publication Nos. cited in ISR.)

Chinese Office Action dated Jan. 4, 2022 in a counterpart Chinese patent application No. 201880082286.9. (A machine translation (not reviewed for accuracy) attached.)

Japanese Office Action dated Feb. 1, 2022 in a counterpart Japanese patent application No. 2017-247051. (A machine translation (not reviewed for accuracy) attached.)

English translation of Written Opinion (PCT/ISA/237) issued in PCT/JP2018/041066 dated Dec. 2018.

Japanese Office Action dated Oct. 12, 2021 in a counterpart Japanese patent application No. 2017-247051. (A machine translation (not reviewed for accuracy) attached.)

Chinese Office Action dated Dec. 5, 2022 in a counterpart Chinese patent application No. 201880082286.9.

Japanese Office Action dated Mar. 14, 2023 in a counterpart Japan patent application No. 2022-076019.

* cited by examiner

SENSING SYSTEM, INFORMATION PROCESSING APPARATUS, AND SENSOR APPARATUS

TECHNICAL FIELD

The present invention relates to a sensing system, an information processing apparatus, and a sensor apparatus.

BACKGROUND ART

In recent years, odor sensor elements have extensively been developed. Known as an odor sensor element is, for example, a quartz crystal microbalance (QCM) sensor in which a film adsorbing an odor-causing substance is provided on the surface of a quartz oscillator. An AT-cut quartz oscillator changes in resonance frequency by a mass change. The QCM sensor detects a change in the resonance frequency by oscillating the AT-cut quartz crystal, and thereby detects the mass of a causing substance.

Also known is a sensor apparatus including a plurality of odor sensor elements detecting the masses of respective different causing substances. Such a sensor apparatus is able to output the mass of each of the causing substances. An information processing apparatus receives the amount of each of the causing substances output from such a sensor apparatus and compares a pattern of the amount of each of the received causing substances with patterns registered in advance. Accordingly, the information processing apparatus is able to identify the type of an odor.

Such a sensor apparatus is combined with information processing technologies such as Internet of Things (IOT) technologies, and can thereby be used for, for example, indoor or in-vehicle environment management, food sanitary management, factory process management, and physical condition management for humans, pets, or the like.

Patent Document 1 and Patent Document 2 each describe a technique providing a notification about a replacement time of a filter of an air purification apparatus. Patent Document 3 describes a technique controlling an in-vehicle environment in accordance with in-vehicle odors.

CITATION LIST

Patent Literature

Patent Document 1: Japanese Laid-open Patent Publication No. H11-156131
Patent Document 2: Japanese Laid-open Patent Publication No. 2000-210518
Patent Document 3: Japanese Laid-open Patent Publication No. 2016-199098

SUMMARY OF INVENTION

Problem to be Solved by Invention

By the way, in-vehicle space is extremely small and hermetically sealed, and occupants stay in there for a long time. Thus, there is a high possibility that the inside of a vehicle has a strong odor. Seat dirt may cause the odor in the in-vehicle space. It is difficult to remove the seat dirt when its cumulative amount increases.

However, the occupants themselves hardly notice that the odor in the in-vehicle space has become stronger by the seat dirt. Consequently, there is a possibility that, when they notice the seat dirt, it is already difficult to remove the seat dirt even by cleaning. Therefore, there is a need for a seat odor to be detected with high accuracy in order to detect the seat dirt and the like.

The present invention has been made in view of the above, and an object thereof is to provide a sensing system, an information processing apparatus, and a sensor apparatus that are capable of detecting odors with high accuracy.

Means for Solving Problem

For solving the above-described problem and achieving an object, a sensing system according to the present invention includes: a sensor apparatus including a filter configured to remove an odor-causing substance contained in air, and a sensor unit including one or more detection elements configured to detect an amount of the odor-causing substance contained in air; and an information processing apparatus including a difference calculation unit configured to calculate a difference between a detection value of each of the one or more detection elements, the detection value indicating an amount of the odor-causing substance contained in air that has passed through the filter, and a detection value of each of the one or more detection elements, the detection value indicating an amount of the odor-causing substance contained in air that has not passed through the filter, and a determination unit configured to determine an odor of air based on the calculated difference.

Effect of Invention

According to the present invention, odors can be detected with high accuracy.

DESCRIPTION OF EMBODIMENTS

The following describes a sensing system 10 according to the present embodiment with reference to the accompanying drawings.

Figure 1:
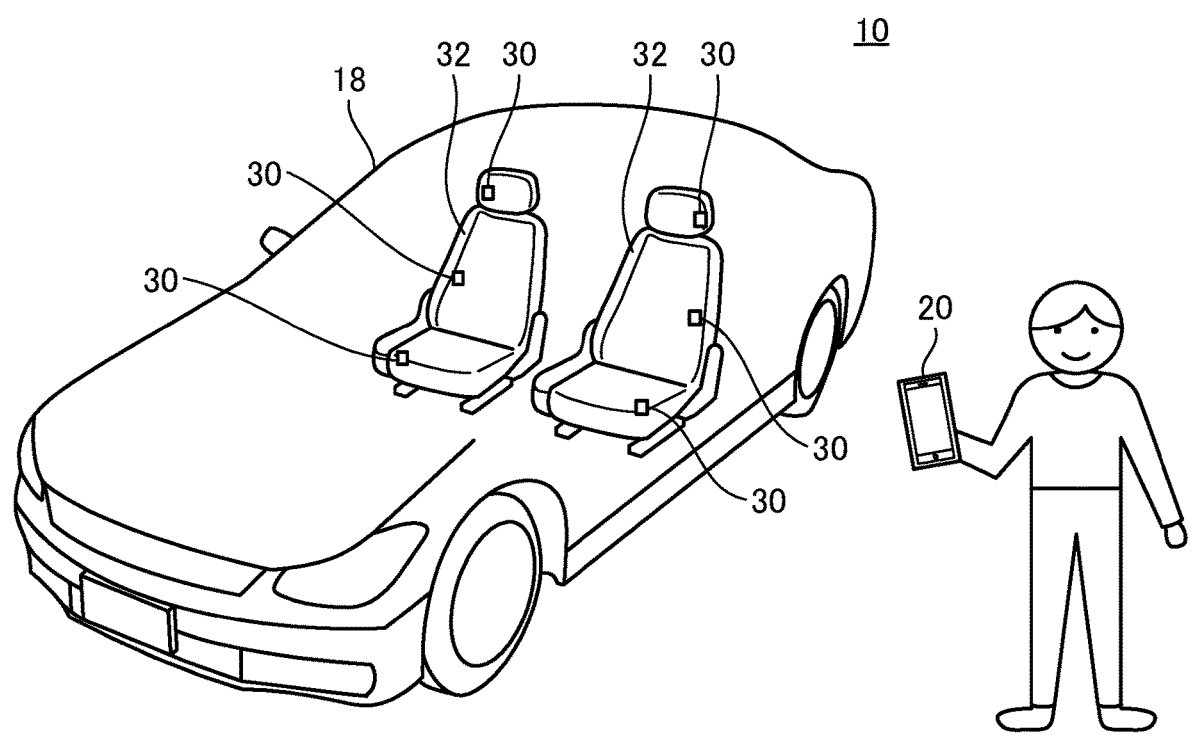
FIG. 1 is a diagram illustrating a sensing system according to an embodiment.

FIG. 1 is a diagram illustrating the sensing system 10 according to the embodiment. The sensing system 10 detects odors from a target object as an odor source with high accuracy. In the present embodiment, the sensing system 10 is applied to a vehicle 18. The sensing system 10 applied to the vehicle 18 detects odors from (in-vehicle) seats 32 in the vehicle 18 as an odor source. The sensing system 10 may be used for not only the seats 32 in the vehicle 18 but also another apparatus. The sensing system 10 may detect odors from a bed, a chair, a toilet, or the like as an odor source, for example.

The sensing system 10 includes an information processing apparatus 20 and one or more sensor apparatuses 30.

The information processing apparatus 20 is a computer having a data processing function, a communication function, and a display function. The information processing apparatus 20 is a smartphone, a tablet, a wearable computer, a cellular phone, or a computer such as a notebook computer, for example. The information processing apparatus 20 may be an exclusive or general-purpose computer provided inside the vehicle 18. The information processing apparatus 20 may be a server or the like that can be connected via a communication apparatus. The information processing apparatus 20 is used by a user (an occupant) using the vehicle 18.

Each of the one or more sensor apparatuses 30 includes the one or more detection elements described above. Each of the one or more detection elements detects the amount of an odor-causing substance contained in air, which causes an odor to be sensed. The detection element detects the mass of the causing substance as the amount of the causing substance. In place thereof, the detection element may detect the volume or the molecular weight of the causing substance as the amount of the causing substance.

The sensor apparatus 30 transmits a signal representing a detection value of each of the one or more incorporated detection elements to the information processing apparatus 20 by wireless communication. The sensor apparatus 30 is able to communicate with the information processing apparatus 20 by a wireless local area network (LAN), such as IEEE 802.11, or near-field wireless communication for digital devices, such as IEEE 802.15, for example. When the information processing apparatus 20 is the exclusive or general-purpose computer provided inside the vehicle 18, the sensor apparatus 30 may transmit the signal representing the detection value of each of the one or more incorporated detection elements to the information processing apparatus 20 with wired communication.

Each of the one or more sensor apparatuses 30 is installed close to the seat 32 in the vehicle 18. The sensor apparatus 30 is installed, for example, closer to any of a seating part, a backrest, and a headrest of the seat 32. Thus, the sensor apparatus 30 is able to detect the amount of the causing substance from the seat 32 (the seating part, the backrest, or the headrest, for example) as an odor source.

In a case that the vehicle 18 includes a plurality of seats 32, the sensing system 10 may include a plurality of sensor apparatuses 30 corresponding to the respective seats 32. The sensing system 10 may include a plurality of sensor apparatuses 30 each corresponding to the seating part, the backrest, and the headrest of the seat 32.

The information processing apparatus 20 receives the signal representing the detection value of each of the one or more detection elements from each of the one or more sensor apparatuses 30. For each of the one or more sensor apparatuses 30, the information processing apparatus 20 detects an odor of ambient air in which the sensor apparatus 30 of interest is installed based on the received detection value of each of the one or more detection elements. The information processing apparatus 20 determines the type and intensity of the odor of the ambient air of the installation position, for example.

The information processing apparatus 20 outputs, based on the detected odor, information representing an odor of the seat 32 (the seating part, the backrest, or the headrest) in which the sensor apparatus 30 is installed. For example, the information processing apparatus 20 outputs information representing the type and intensity of odor of the seat 32 (the seating part, the backrest, or the headrest) in which the sensor apparatus 30 is installed. Furthermore, the information processing apparatus 20 may estimate and output, based on an odor determination result in the past, a time for cleaning the seat 32 (the seating part, the backrest, or the headrest) in which the sensor apparatus 30 is installed.

Figure 2:
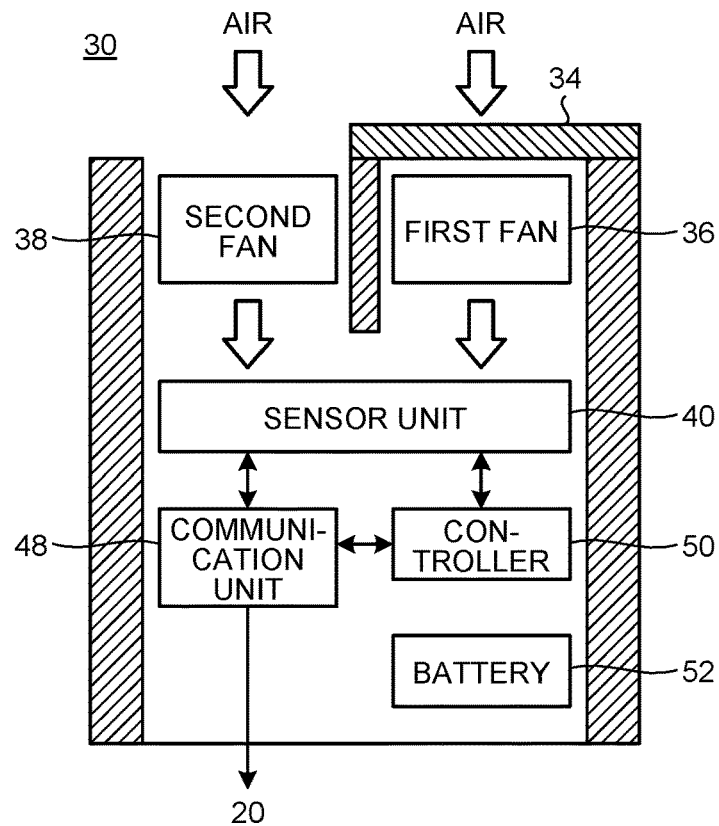
FIG. 2 is a diagram illustrating a configuration of a sensor apparatus.

FIG. 2 is a diagram illustrating a configuration of the sensor apparatus 30. The sensor apparatus 30 has a size small enough to be portable with one hand, for example. The sensor apparatus 30 is housed in a casing that has a size with one side being about a few millimeters to a few centimeters, for example. The shape of the sensor apparatus 30 is by way of example and may have any shape.

The sensor apparatus 30 includes a filter 34, a first fan 36, a second fan 38, a sensor unit 40, a communication unit 48, a controller 50, and a battery 52.

The filter 34 passes air therethrough and removes an odor-causing substance from air that has been passed. The filter 34 removes one or more odor-causing substances as objects to be detected. The filter 34 may remove partial odor-causing substances of the one or more odor-causing substances as the objects to be detected.

The first fan 36 takes in air, causes the air to pass through the filter 34, and supplies the air to the sensor unit 40. The first fan 36 is provided, for example, between the filter 34 and the sensor unit 40 and sends air, which has passed through the filter 34, out to the sensor unit 40. The sensor apparatus 30 is placed such that an air intake port of the first fan 36 is positioned near the target object (the seating part, the backrest, or the headrest of the seat 32, for example). The first fan 36 takes in air from the vicinity of the target object, causes the air to pass through the filter 34, and supplies the air to the sensor unit 40. Thus, the first fan 36 is able to take in air containing minute substances attached to the target object, cause the air to pass through the filter 34, and supply the air to the sensor unit 40.

The second fan 38 takes in air, causes the air not to pass through the filter 34, and supplies the air to the sensor unit 40. The second fan 38 is provided, for example, between an air intake port and the sensor unit 40 and sends air, which has not passed through the filter 34, out to the sensor unit 40. The sensor apparatus 30 is placed such that the air intake port of the second fan 38 is positioned near the target object (the seating part, the backrest, or the headrest of the seat 32, for example). The second fan 38 takes in air from the vicinity of the target object, causes the air not to pass through the filter 34, and supplies the air to the sensor unit 40. Thus, the second fan 38 is able to take in air containing minute substances attached to the target object, cause the air not to pass through the filter 34, and supply the air to the sensor unit 40.

The sensor unit 40 includes the one or more detection elements described above. The air having passed through the filter 34 and the air having not passed through the filter 34 are given to the sensor unit 40 at different timings. Each of the one or more detection elements detects the amount of the odor-causing substance when the air having passed through the filter 34 is given. Furthermore, each of the one or more detection elements also detects the amount of the odor-causing substance when the air having not passed through the filter 34 is given.

The sensor unit 40 outputs a detection value of each of the one or more detection elements, the detection value indicating an amount of the odor-causing substance contained in air that has passed through the filter 34, and outputs a detection value of each of the one or more detection elements, the detection value indicating the amount of the odor-causing substance contained in air that has not passed through the filter 34. Specifically, the sensor unit 40 outputs the detection value of each of the one or more detection elements when air, which has been blown from the first fan 36 and has passed through the filter 34, is given, and outputs the detection value of each of the one or more detection elements when air, which has been blown from the second fan 38 and has not passed through the filter 34, is given.

In a case that the sensor unit 40 includes a plurality of detection elements, those detection elements are different types of elements.

For example, any two detection elements included in the sensor unit 40 detect the amounts of different types of odor-causing substances. While a first detection element detects the amount of a substance X, a second detection element detects the amount of a substance Y, for example. Any two detection elements included in the sensor unit 40 may detect the amount of the same type of odor-causing substance with different sensitivities, for example. While a first detection element detects the amount of the substance X with a first sensitivity, a second detection element detects the amount of the substance X with a second sensitivity, which is lower than the first sensitivity, for example.

Any two detection elements included in the sensor unit 40 may detect the amounts of a plurality of odor-causing substances of different types of combinations, for example. While a first detection element detects the total amount of the substance X and the substance Y, a second detection element detects the total amount of the substance X and a substance Z, for example. Any two detection elements included in the sensor unit 40 may detect the amounts of a plurality of odor-causing substances of the same type of combination with different sensitivities, for example. While a first detection element may detect the total amount of the substance X and the substance Y with the first sensitivity, a second detection element may detect the total amount of the substance X and the substance Y with the second sensitivity, which is lower than the first sensitivity, for example.

The communication unit 48 transmits a signal detected by the sensor unit 40 to the information processing apparatus 20. That is to say, to the information processing apparatus 20, the communication unit 48 transmits: a signal representing the detection value of each of the one or more detection elements, which indicates the amount of the odor-causing substance contained in air having passed through the filter 34; and a signal representing the detection value of each of the one or more detection elements, which indicates the amount of the odor-causing substance contained in air having not passed through the filter 34.

The controller 50 manages and controls operation of the first fan 36, the second fan 38, the sensor unit 40, and the communication unit 48. The controller 50 controls operation start timings and operation end timings of the first fan 36 and the second fan 38, for example.

The battery 52 supplies operating electric power to the first fan 36, the second fan 38, the communication unit 48, and the controller 50. The sensor apparatus 30 may be provided with, in place of the battery 52, an electric power acquisition unit to acquire an electric power source installed in the vehicle 18. The electric power acquisition unit supplies operating electric power to the first fan 36, the second fan 38, the sensor unit 40, the communication unit 48, and the controller 50.

Figure 3:
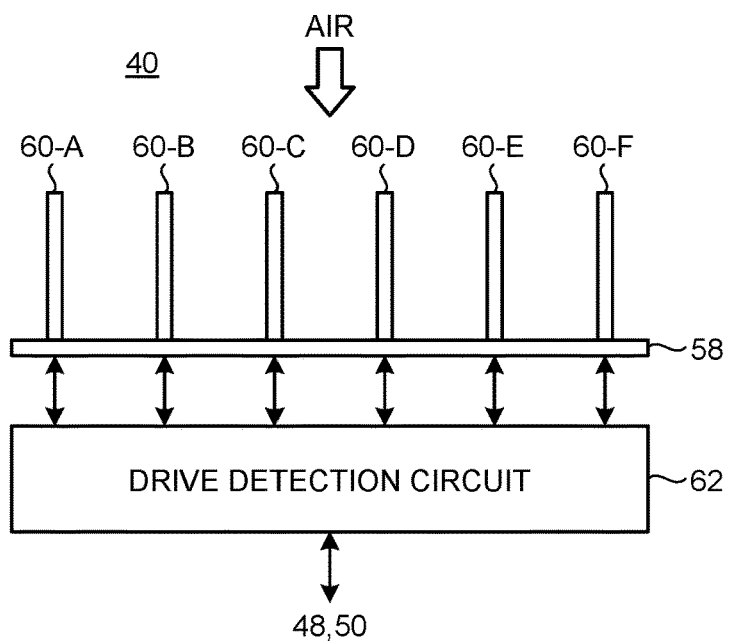
FIG. 3 is a diagram illustrating an exemplary configuration of a sensor unit.

FIG. 3 is a diagram illustrating a configuration of the sensor unit 40. In the present embodiment, the sensor unit 40 is a quartz crystal microbalance (QCM) sensor that is able to detect the mass of minute substances contained in air. The sensor unit 40 is not limited to the QCM sensor but may be another type of sensor such as a gas sensor including a semiconductor thin film.

In the present embodiment, the sensor unit 40 includes a support 58, one or more gas detection elements 60, and a drive detection circuit 62. Each of the one or more gas detection elements 60 is attached to the support 58.

The gas detection elements 60 are exemplary detection elements. In the example in FIG. 3, the sensor unit 40 has six different types of gas detection elements 60-A to 60-F. The six gas detection elements 60-A to 60-F detect respective different types of odor-causing substances, for example.

Each of the one or more gas detection elements 60 includes a quartz oscillator that is cut so as to be oscillatable by the piezoelectric effect, two electrodes provided on planes on both sides of the quartz oscillator, and an adsorption film provided on at least one of the planes of the quartz oscillator.

Part of a side face of the quartz oscillator is oscillatably held by the support 58. An AC voltage is applied from the drive detection circuit 62 to the two electrodes. The adsorption film adsorbs a specific causing substance contained in the ambient air. The one or more gas detection elements 60 include adsorption films adsorbing respective different substances. Specifically, each of the one or more gas detection elements 60 includes the adsorption film adsorbing a causing substance as an object to be detected of the sensor apparatus 30.

In such a gas detection elements 60, when an AC voltage with a resonance frequency is applied to the two electrodes, the quartz oscillator oscillates by the piezoelectric effect. The fundamental resonance frequency of the quartz oscillator is determined by mass and viscoelasticity. Consequently, when the adsorption film adsorbs the causing substance thereby changing the mass, the gas detection elements 60 change in the fundamental resonance frequency in accordance with the change in the mass due to adsorption.

When the first fan 36 or the second fan 38 blows, the drive detection circuit 62 applies an AC voltage to each of the one or more gas detection elements 60 and detects a change in the fundamental resonance frequency of each of the one or more gas detection elements 60. Thus, the drive detection circuit 62 is able to detect the mass of the odor-causing substance contained in air given by blowing by the first fan 36 or the second fan 38 for each of the one or more gas detection elements 60. The drive detection circuit 62 gives a detection value to the communication unit 48.

Figure 4:
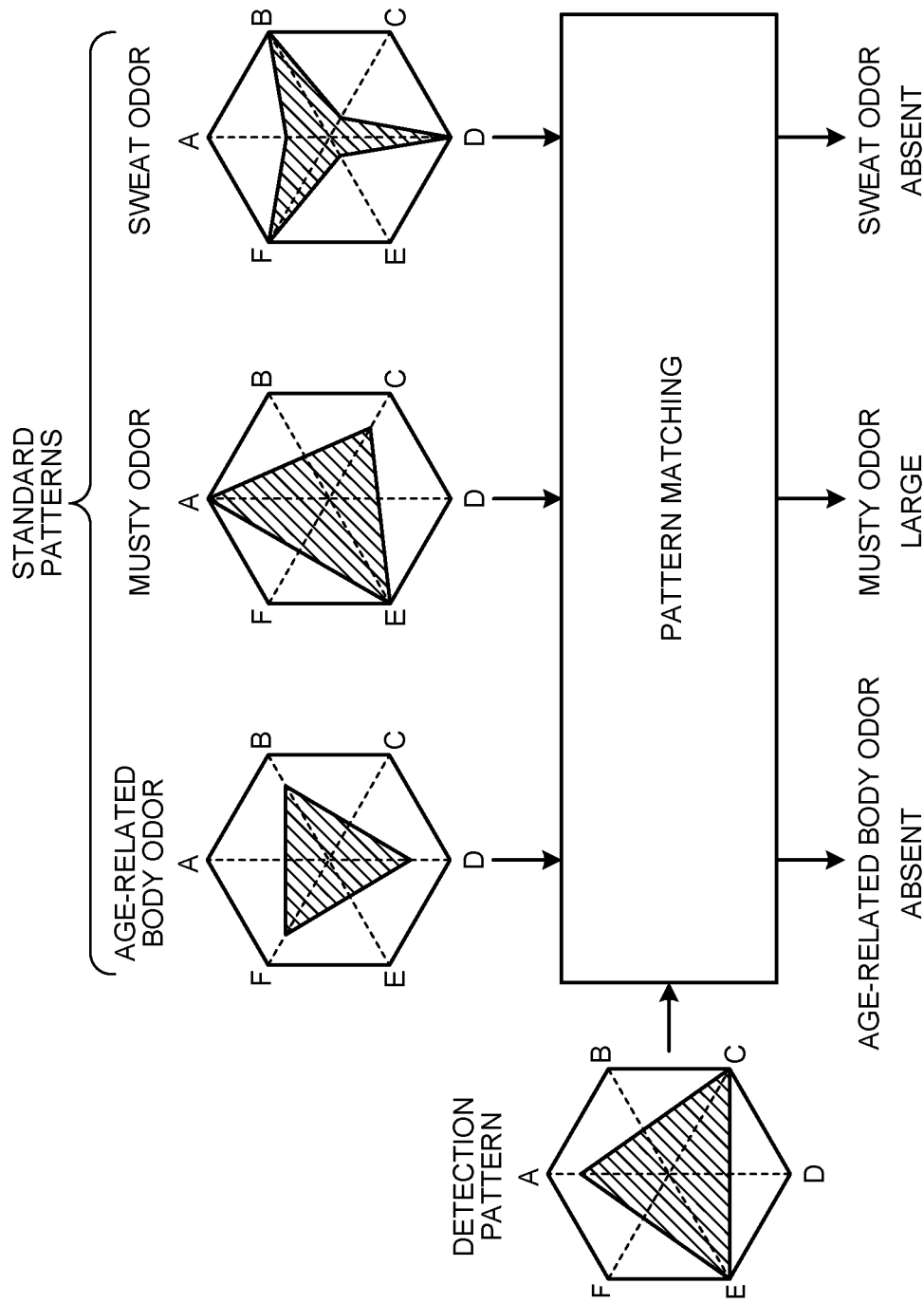
FIG. 4 is a diagram for explaining odor determination processing.

FIG. 4 is a diagram for explaining odor determination processing.

The information processing apparatus 20 acquires the signal representing the detection value of each of the one or more detection elements from the sensor apparatus 30. In the example in FIG. 4, the information processing apparatus 20 acquires the signal representing the detection value of each of the gas detection element 60-A, the gas detection element 60-B, the gas detection element 60-C, the gas detection element 60-D, the gas detection element 60-E, and the gas detection element 60-F.

The information processing apparatus 20 stores a standard pattern representing the detection value of each of the one or more detection elements, which is acquired when a given type odor occurs. In the example in FIG. 4, the information processing apparatus 20 stores standard patterns each representing the detection value of each of the gas detection elements 60-A to F acquired when each of an age-related body odor, a musty odor, and a sweat odor is detected.

The information processing apparatus 20 performs matching between: a detection pattern representing the detection value of each of the one or more detection elements contained in the signal acquired from the sensor apparatus 30; and the standard pattern representing the detection value of each of the one or more detection elements when the given type of odor stored in advance occurs. When the detection pattern acquired from the sensor apparatus 30 matches the standard pattern, the information processing apparatus 20 determines that the odor of air given to the sensor apparatus 30 is the given type of odor. The information processing apparatus 20 may store standard patterns for a plurality of types of odors and determine whether one detection pattern matches the standard pattern of either one of the odors. In the example in FIG. 4, the information processing apparatus 20 determines that the odor of air given to the sensor apparatus 30 is the musty odor.

Furthermore, the information processing apparatus 20 may also determine, for each type of odor, the intensity of odor by matching. The information processing apparatus 20 may store the standard pattern for each type of odor and each intensity of odor and perform matching between the detection pattern acquired from the sensor apparatus 30 and the strand pattern for each type of odor and each intensity of odor stored in advance, for example.

The information processing apparatus 20 may update the standard patterns stored in advance by learning processing using a detection pattern as teacher data, which is obtained when a user smells the given type of odor. The information processing apparatus 20 may regularly acquire a plurality of standard patterns for each type of odor and each intensity of odor from a server or the like and update the stored standard pattern.

The information processing apparatus 20 may determine the type and intensity of the odor by another method in place of such pattern matching. The information processing apparatus 20 may determine the type of the odor and the intensity of odor using a technique such as a neural network, for example.

The example in FIG. 4 illustrates that the sensor apparatus 30 outputs the detection values of the six types of gas detection elements 60-A to 60-F. However, the sensor apparatus 30 may output detection values of less than six types of or more than six types of detection elements. The example in FIG. 4 illustrates that the age-related body odor, the musty odor, and the sweat odor are determined. However, the information processing apparatus 20 may determine odors other than those ones. The sensor apparatus 30 of the present embodiment may output a detection value of one detection element.

The sensor apparatus 30 outputs: the detection value of each of the one or more detection elements, which indicates the amount of the odor-causing substance contained in air that has passed through the filter 34; and the detection value of each of the one or more detection elements, which indicates the amount of the odor-causing substance contained in air that has not passed through the filter 34. The sensor apparatus 30 outputs these detection values to the information processing apparatus 20.

The information processing apparatus 20 calculates a difference pattern representing the difference between a first pattern and a second pattern. The first pattern represents the detection value of each of the one or more detection elements, which indicates the amount of the odor-causing substance contained in air having passed through the filter 34. The second pattern represents the detection value of each of the one or more detection elements, which indicates the amount of the odor-causing substance contained in air having not passed through the filter 34. The information processing apparatus 20 detects the odor of air based on the difference pattern. The information processing apparatus 20 determines the type and intensity of the odor of air by, for example, performing matching on the difference pattern against the standard patterns stored in advance.

Figure 5:
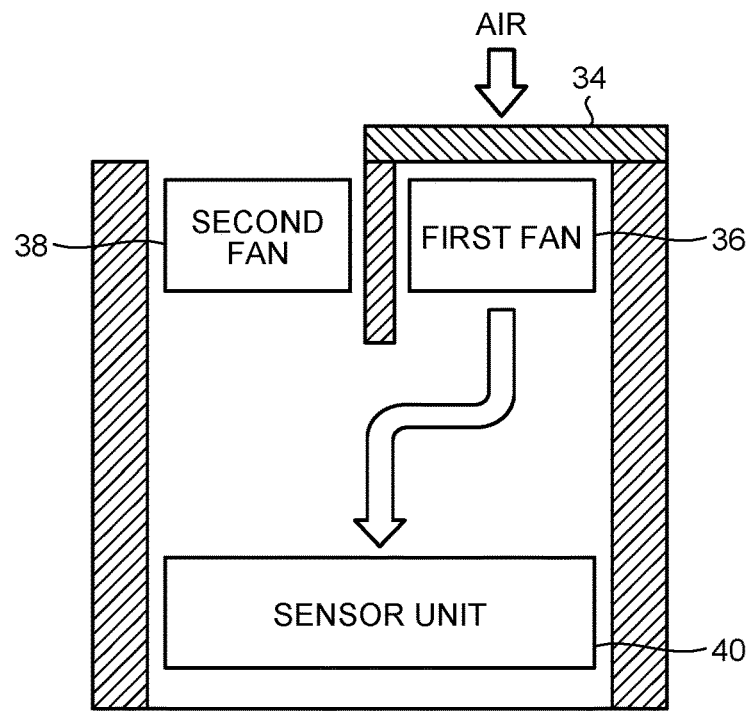
FIG. 5 is a diagram illustrating an air flow in a first mode.

FIG. 5 is a diagram illustrating an air flow in a first mode. The controller 50 of the sensor apparatus 30 switches between the first mode and a second mode at the time of odor detection. In the first mode, the controller 50 causes the first fan 36 to operate and causes the second fan 38 to stop. In the first mode, the sensor unit 40 detects the amount of the odor-causing substance from air blown from the first fan 36 by using each of the one or more incorporated detection elements. Thus, the sensor unit 40 is able to output the detection value of each of the one or more detection elements, which indicates the amount of the odor-causing substance contained in air that has passed through the filter 34.

Figure 6:
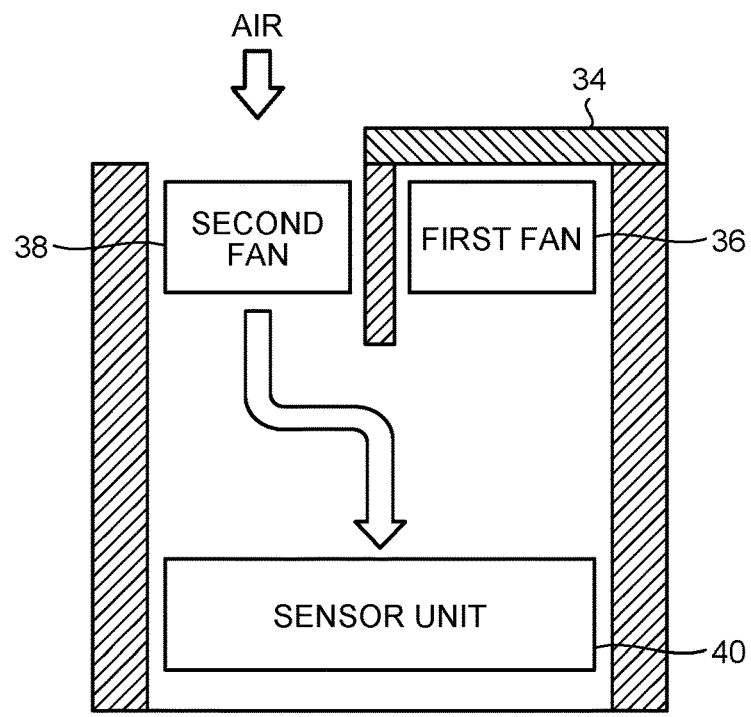
FIG. 6 is a diagram illustrating an air flow in a second mode.

FIG. 6 is a diagram illustrating an air flow in the second mode. In the second mode, the controller 50 causes the first fan 36 to stop and causes the second fan 38 to operate. In such a second mode, the sensor unit 40 detects the amount of the odor-causing substance from air blown from the second fan 38 by using each of the one or more incorporated detection elements. Thus, the sensor unit 40 is able to output the detection value of each of the one or more detection elements, which indicates the amount of the odor-causing substance contained in air that has not passed through the filter 34.

Figure 7:
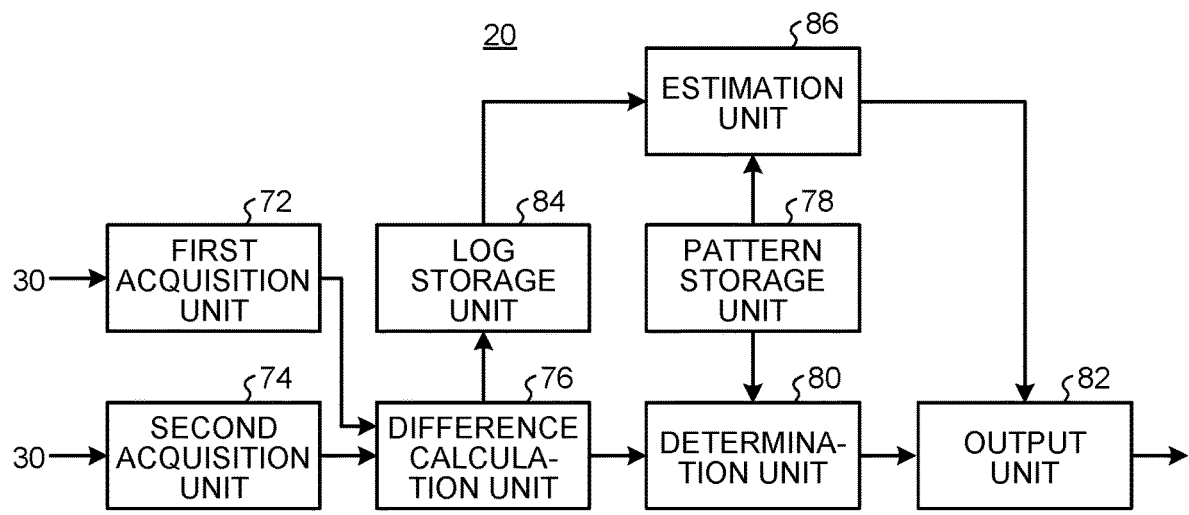
FIG. 7 is a diagram illustrating a functional configuration of an information processing apparatus.

FIG. 7 is a diagram illustrating a functional configuration of the information processing apparatus 20. The information processing apparatus 20 implements functions of each block illustrated in FIG. 7 by executing a given application program.

The information processing apparatus 20 implementing such functions includes a first acquisition unit 72, a second acquisition unit 74, a difference calculation unit 76, a pattern storage unit 78, a determination unit 80, an output unit 82, a log storage unit 84, and an estimation unit 86.

The first acquisition unit 72 acquires, from the sensor apparatus 30, the signal representing the detection value of each of the one or more detection elements, which indicates the amount of the odor-causing substance contained in air that has passed through the filter 34. The second acquisition unit 74 acquires, from the sensor apparatus 30, the signal representing the detection value of each of the one or more detection elements, which indicates the amount of the odor-causing substance contained in air that has not passed through the filter 34. The first acquisition unit 72 and the second acquisition unit 74 may be implemented by common hardware or implemented by separate pieces of hardware.

The difference calculation unit 76 calculates the difference pattern representing the difference between the first pattern representing the detection value of the one or more detection elements acquired by the first acquisition unit 72 and the second pattern representing the detection value of the one or more detection elements acquired by the second acquisition unit 74. That is to say, the difference calculation unit 76 calculates the difference pattern representing the difference between: the first pattern representing the detection value of each of the one or more detection elements, which indicates the amount of the odor-causing substance contained in air that has passed through the filter 34; and the second pattern representing the detection value of each of the one or more detection elements, which indicates the amount of the odor-causing substance contained in air that has not passed through the filter 34.

The difference calculation unit 76 subtracts, from the detection value of each of the one or more detection elements included in the second pattern, the detection value of the corresponding detection element included in the first pattern. The calculated difference pattern represents a detection value of each of the one or more detection elements, from which error components, such as noise occurring caused by adsorption of substances other than the causing substance to the adsorption film and the like, and an offset of the sensor apparatus 30 have been removed.

The pattern storage unit 78 stores one or more standard patterns in association with each of a plurality of types of odors. The standard pattern represents the detection value indicating the amount of the odor-causing substance contained in air of a corresponding type of odor of each of the one or more detection elements. For example, the pattern storage unit 78 stores the standard pattern representing the detection value of each of the one or more detection elements acquired by the sensor apparatus 30 when the age-related body odor, the musty odor, and the sweat odor are respectively detected. The pattern storage unit 78 may store not only such types of odors but also patterns of other odors. Furthermore, the pattern storage unit 78 may store the standard pattern for each intensity of odor for each type of odor.

The determination unit 80 performs matching between the difference pattern and the one or more standard patterns stored in the pattern storage unit 78. When the difference pattern matches any of the standard patterns, the determination unit 80 determines that the odor of air is any type of odor. More specifically, the determination unit 80 selects any standard pattern that matches or is within a given range of the difference pattern out of the one or more standard patterns. The determination unit 80 then determines that the odor of air is the odor of the type corresponding to the selected standard pattern.

The case in which patterns match each other represents not only a case in which two patterns completely match each other but also a case in which they match each other with a given error or less and a case in which the closest standard pattern out of a plurality of standard patterns is selected. Furthermore, the determination unit 80 may determine, for each type of odor, the intensity of odor. Thus, the determination unit 80 is able to determine the type of the odor and the intensity of odor. The determination unit 80 may determine the type of the odor and the intensity of odor by not only such pattern matching but also another method. The determination unit 80 may determine the type of the odor and the intensity of odor matching the difference pattern by using a neural network or the like, for example.

The output unit 82 outputs information representing the odor of air determined by the determination unit 80. The output unit 82 outputs the type of the odor and the intensity of odor, for example. The output unit 82 causes a display unit to display the type of the odor and the intensity of odor that have been determined, for example. The output unit 82 may output the information representing the type of the odor and the intensity of odor by voice or transmit the information to another apparatus over a network. The output unit 82 may determine the degree of dirt of the seat 32 (the seating part, the backrest, or the headrest, for example) as the target object based on the type of the odor and the intensity of odor of the source of the odor and display the determined degree of dirt.

The log storage unit 84 stores the difference pattern calculated by the difference calculation unit 76 in association with an acquisition time of the detection value of each of the one or more detection elements serving as a base of the difference pattern. Furthermore, the log storage unit 84 also stores the difference pattern calculated in the past and the acquisition time in association with each other. The log storage unit 84 may store the first pattern and the second pattern in place of the difference pattern.

The estimation unit 86 estimates a difference pattern, which is predicted to be calculated at any time, based on the difference pattern and the corresponding acquisition time stored in the log storage unit 84. The estimation unit 86 estimates, based on, for example, one or more difference patterns before any first time, the difference pattern at the first time. The estimation unit 86 identifies, for each of a plurality of difference detection values included in the difference pattern, a function representing a temporal change in the difference detection value and substitutes the first time into the identified function. Thus, the estimation unit 86 is able to estimate the difference pattern at the first time.

Furthermore, the estimation unit 86 estimates an odor occurring at the first time by performing matching between the difference pattern at the first time and the patterns stored in the pattern storage unit 78. The estimation unit 86 estimates the type and intensity of the odor at the first time, for example.

When the estimation unit 86 estimates the odor occurring at the first time, the output unit 82 outputs an estimation result of the odor occurring at the first time. For example, the output unit 82 causes the display unit to display the estimation result of the odor occurring at the first time.

Furthermore, the estimation unit 86 may estimate a time at which the given type of odor occurs based on a plurality of difference patterns and a plurality of corresponding acquisition times stored in the log storage unit 84. The estimation unit 86 estimates a time at which the given type of odor reaches a given intensity, for example. In this case, the estimation unit 86 identifies the function representing a temporal change in the difference detection value for each of the difference detection values included in the difference pattern. Based on the function representing a temporal change in each of the difference detection values, a time at which the pattern of the difference detection values matches the pattern stored in the pattern storage unit 78 is calculated.

When the estimation unit 86 estimates the time at which the given type of odor occurs, the output unit 82 outputs the time at which the given type of odor occurs. For example, the output unit 82 causes the display unit to display the time at which the given type of odor occurs. The output unit 82 may output information for prompting replacement or cleaning of the seat 32 (the seating part, the backrest, or the headrest, for example) as the target object at the time at which the given type of odor occurs.

In a case that the sensing system 10 includes a plurality of sensor apparatuses 30, the information processing apparatus 20 causes each of the sensor apparatuses 30 to execute the processing by each block. The information processing apparatus 20 may cause the sensor apparatuses 30 to acquire the first pattern and the second pattern for each given time and cause the sensor apparatuses 30 to execute the processing by each block based on the first pattern and the second pattern that have been acquired for each given time.

Figure 8:
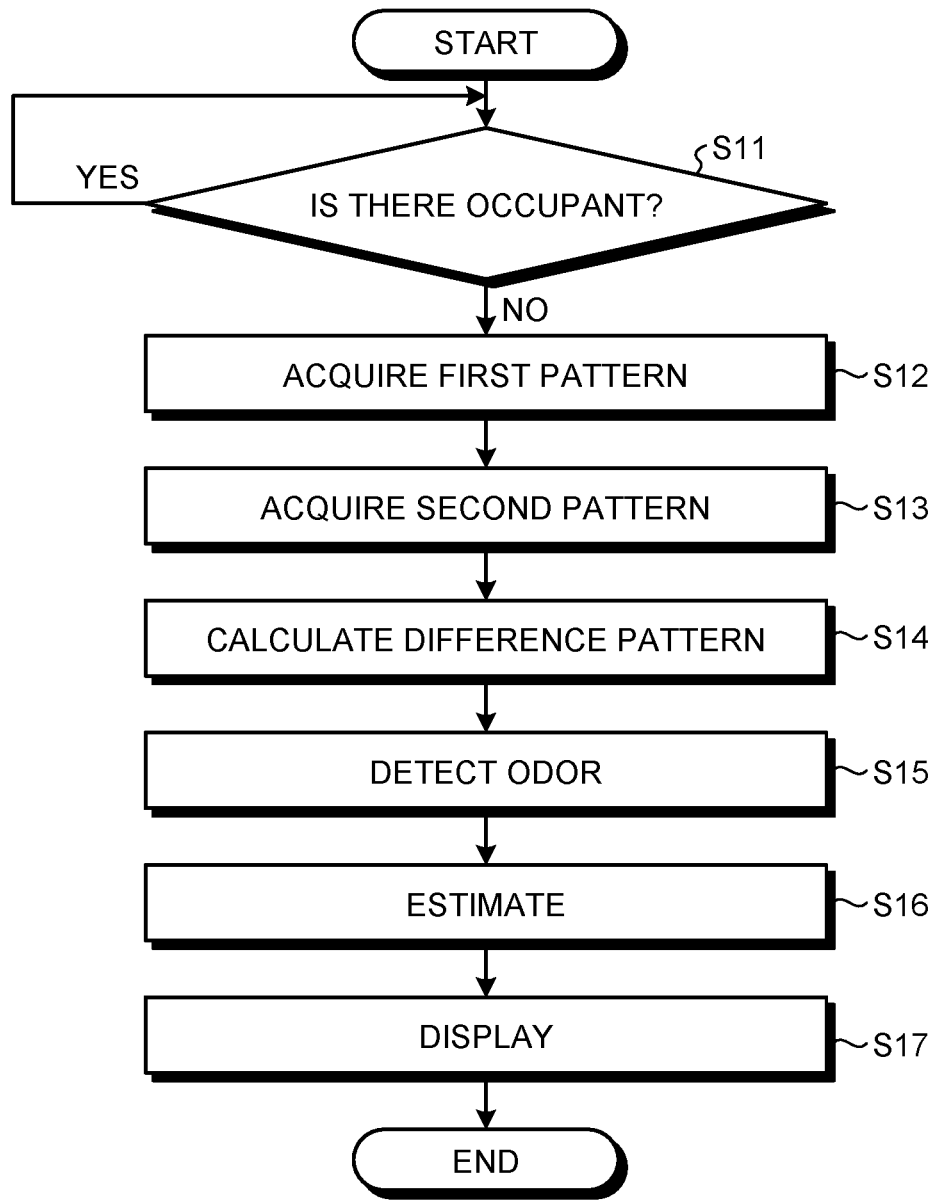
FIG. 8 is a flowchart of an exemplary procedure of odor detection processing by the information processing apparatus.

FIG. 8 is a flowchart of an exemplary procedure of odor detection processing by the information processing apparatus 20. The information processing apparatus 20 executes, for example, the processes from Step S11 to Step S17 in FIG. 8 for each of the sensor apparatuses 30 and for each given time. The information processing apparatus 20 executes the processes from Step S11 to Step S17 in FIG. 8 about once a day with a timing when the vehicle 18 is not used, or at midnight or early in the morning, for example.

First, at Step S11, the information processing apparatus 20 determines whether an occupant is present in the vehicle 18. When there is an occupant in the vehicle 18 (Yes at Step S11), the information processing apparatus 20 is on standby at Step S11 or ends the flow.

When there is no occupant in the vehicle 18 (No at step S11), the information processing apparatus 20 advances the process to Step S12. At Step S12, the information processing apparatus 20 acquires, from the sensor apparatus 30, the first pattern representing the detection value of each of the one or more detection elements, which indicates the amount of the odor-causing substance contained in air that has passed through the filter 34. Subsequently, at Step S13, the information processing apparatus 20 acquires, from the sensor apparatus 30, the second pattern representing the detection value of each of the one or more detection elements, which indicates the amount of the odor-causing substance contained in air that has not passed through the filter 34.

Subsequently, at Step S14, the information processing apparatus 20 calculates the difference pattern representing the difference between the first pattern and the second pattern. For example, the information processing apparatus 20 subtracts, from the detection value of each of the one or more detection elements included in the second pattern, the detection value of each of the corresponding detection elements included in the first pattern to calculate the difference pattern.

Subsequently, at Step S15, the information processing apparatus 20 performs matching on the difference pattern against the standard pattern to detect an odor. The information processing apparatus 20 determines the type of the odor and the intensity of odor, for example.

Subsequently, at Step S16, the information processing apparatus 20 estimates a time at which the given type of odor reaches a given intensity of odor, based on a plurality of difference patterns calculated in the past and a plurality of corresponding acquisition times.

Subsequently, at Step S17, the information processing apparatus 20 outputs information representing the determined odor. For example, the information processing apparatus 20 displays, on the display unit, information representing the type and intensity of the determined odor. Furthermore, at Step S17, the information processing apparatus 20 displays the time at which the given type of odor reaches the given intensity of odor.

Upon ending the process at Step S17, the information processing apparatus 20 ends the present flow. In the case that the sensing system 10 includes a plurality of sensor apparatuses 30, the information processing apparatus 20 executes the above processing for each of the sensor apparatuses 30. The information processing apparatus 20 repeatedly executes the above processing for each given time.

Figure 9:
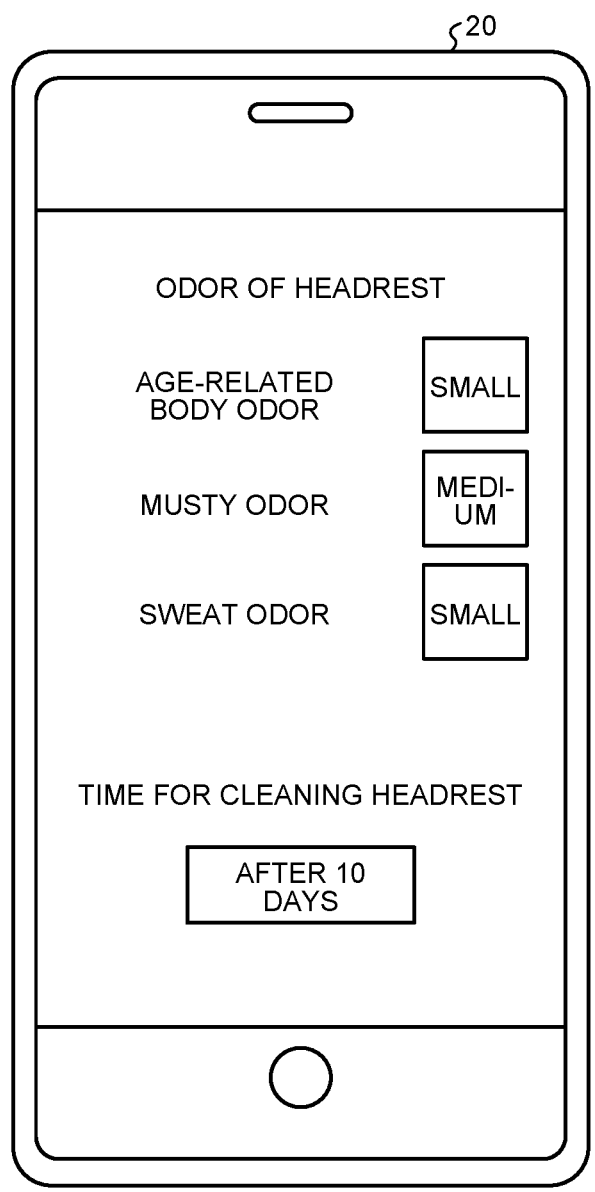
FIG. 9 is a diagram illustrating a display example of the information processing apparatus.

FIG. 9 is a diagram illustrating a display example of the information processing apparatus 20. When the processes from Step S11 to Step S17 on the sensor apparatus 30 installed in the headrest of the seat 32 have been executed, the information processing apparatus 20 displays such an image as illustrated in FIG. 9, for example.

The information processing apparatus 20 determines, for example, whether the age-related body odor, the musty odor, and the sweat odor are occurring. Furthermore, the information processing apparatus 20 also determines the intensity of odor of each of the age-related body odor, the musty odor, and the sweat odor. The information processing apparatus 20 displays information representing the intensity of odor of each of the age-related body odor, the musty odor, and the sweat odor.

The information processing apparatus 20 estimates a time at which any of the age-related body odor, the musty odor, and the sweat odor reaches a given intensity. The information processing apparatus 20 displays the estimated time as information representing a time for cleaning the headrest.

Figure 10:
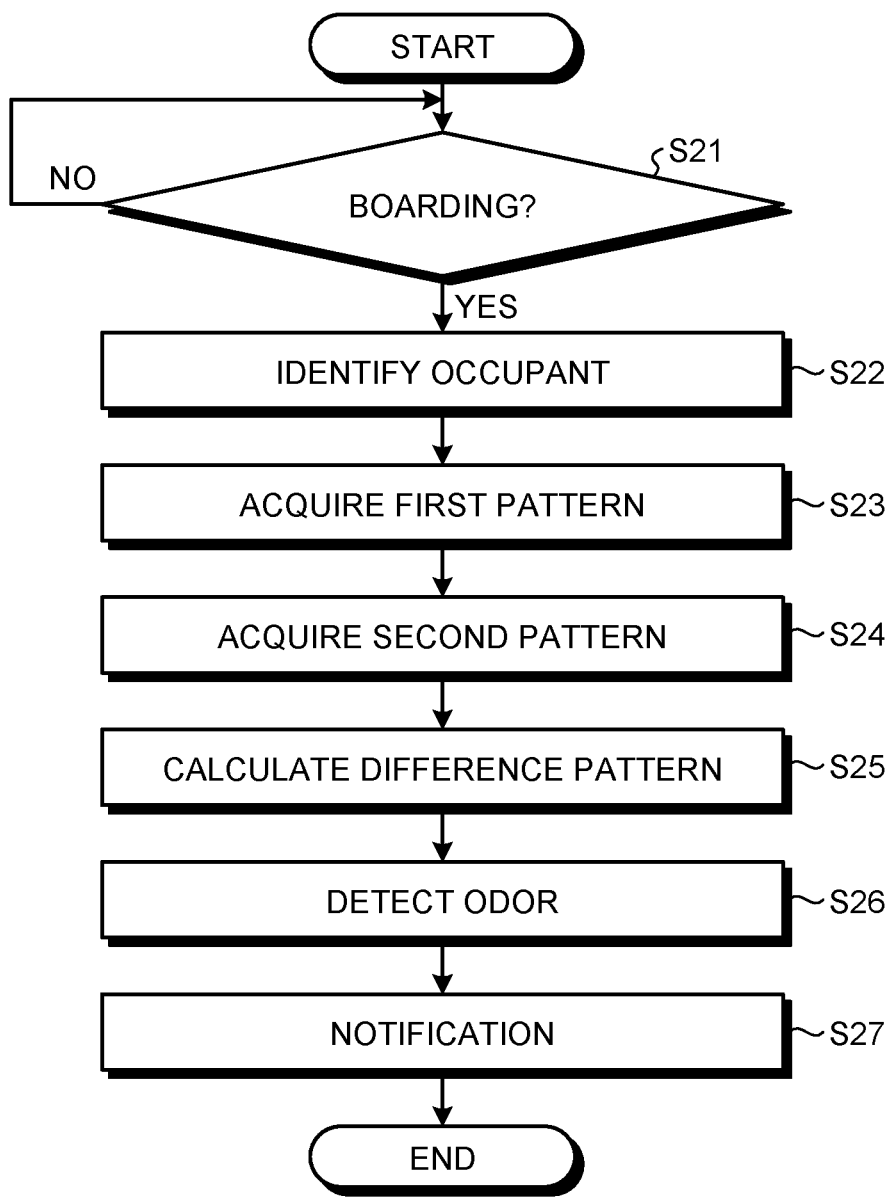
FIG. 10 is a flowchart of a procedure of occupant's odor detection processing by the information processing apparatus.

FIG. 10 is a flowchart of a procedure of occupant's odor detection processing by the information processing apparatus 20. The information processing apparatus 20 may further determine an odor of an occupant by executing the processes from Step S21 to Step S27 in FIG. 10.

At Step S21, the information processing apparatus 20 determines whether an occupant boards the vehicle 18. The information processing apparatus 20 determines, as a timing at which the occupant boards the vehicle 18, a timing at which a door is opened using a key, a timing at which the vehicle 18 is started up using the key, or a timing at which a steering wheel is gripped, for example.

When the occupant does not board the vehicle 18 (No at Step S21), the information processing apparatus 20 is on standby at Step S21. When the occupant boards the vehicle 18 (Yes at Step S21), the information processing apparatus 20 advances the process to Step S22.

At Step S22, the information processing apparatus 20 identifies the occupant. For example, the information processing apparatus 20 may perform face authentication, iris authentication, or the like, based on an image taken by an in-vehicle camera or the like installed in the vehicle 18 to authenticate whether the occupant is a user registered in advance. The information processing apparatus 20 may perform fingerprint authentication based on an image taken by a fingerprint image sensor installed in the vehicle 18 to authenticate whether the occupant is the user registered in advance, for example.

When authentication succeeds, the information processing apparatus 20 performs the processes at Step S23 and the subsequent steps. When authentication fails, the information processing apparatus 20 may end the processing at Step S22 or perform the processes at Step S23 and the subsequent steps without identifying the occupant.

At Step S23, the information processing apparatus 20 acquires, from the sensor apparatus 30, the first pattern representing the detection value of each of the one or more detection elements, which indicates the amount of the odor-causing substance contained in air that has passed through the filter 34. Subsequently, at Step S24, the information processing apparatus 20 acquires, from the sensor apparatus 30, the second pattern representing the detection value of each of the one or more detection elements, which indicates the amount of the odor-causing substance contained in air that has not passed through the filter 34.

Subsequently, at Step S25, the information processing apparatus 20 calculates the difference pattern representing the difference between the first pattern and the second pattern. The information processing apparatus 20 may calculate a double difference pattern representing the difference between the difference pattern with a timing when the occupant has gotten into the vehicle 18 and the difference pattern before the occupant gets into the vehicle 18 (when the occupant is absent). Thus, the information processing apparatus 20 is able to detect the odor increased by the occupant getting into the vehicle 18 with higher accuracy.

Subsequently, at Step S26, the information processing apparatus 20 performs matching between the difference pattern (or the double difference pattern) and the standard pattern to detect an odor. The information processing apparatus 20 determines the type of the odor and the intensity of odor, for example.

Subsequently, at Step S27, the information processing apparatus 20 notifies an application program for health care of information representing the determined odor of air, together with user information on the identified occupant, for example. Then, the application program for health care stores the acquired information representing the odor in association with the user information. The application program for health care may determine the physical condition or health condition of the occupant based on the acquired information representing the odor and display a determination result.

Figure 11:
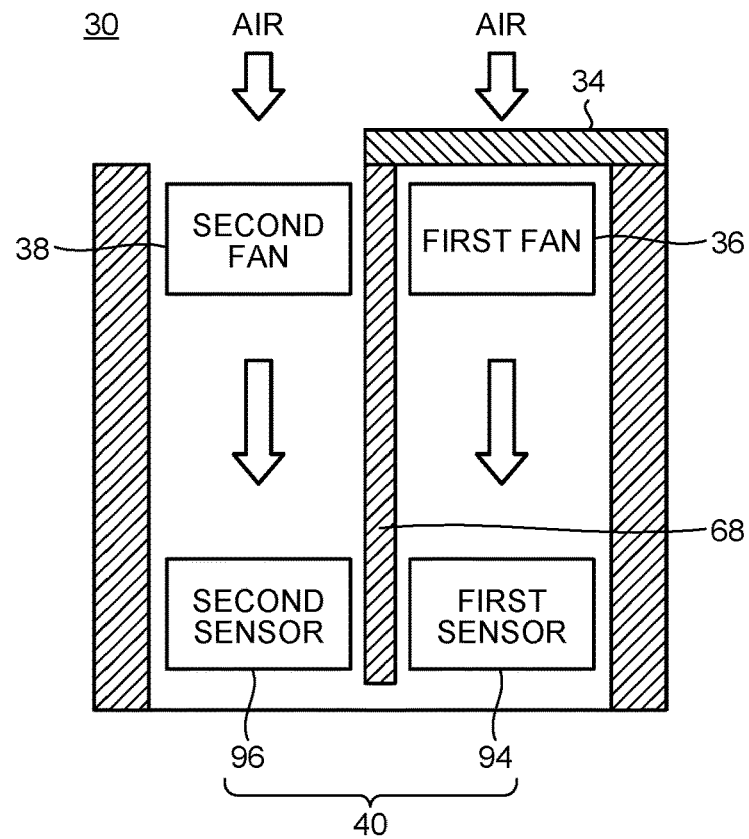
FIG. 11 is a diagram illustrating a partial configuration of the sensor apparatus according to a modification.

FIG. 11 is a diagram illustrating a partial configuration of the sensor apparatus 30 according to a modification. The sensor unit 40 may have a configuration illustrated in FIG. 11 in place of the configuration illustrated in FIG. 2. The sensor unit 40 according to the modification illustrated in FIG. 11 includes a first sensor 94 and a second sensor 96. Each of the first sensor 94 and the second sensor 96 has the same configuration as that of the sensor unit 40 illustrated in FIG. 3.

In the modification, the first fan 36 takes in air from the outside, causes the air to pass through the filter 34, and supplies the air to the first sensor 94. The second fan 38 takes in air from the outside, cause the air not to pass through the filter 34, and supplies the air to the second sensor 96. That is to say, the air having passed through the filter 34 is supplied to the first sensor 94, whereas it is not supplied to the second sensor 96. The air having not passed through the filter 34 is supplied to the second sensor 96, whereas it is not supplied to the first sensor 94. The sensor apparatus 30 according to the modification includes, for example, a wall 68 that separates the first fan 36 and the first sensor 94 from the second fan 38 and the second sensor 96.

The first sensor 94 detects the amount of the odor-causing substance contained in air blown from the first fan 36 by using each of one or more incorporated detection elements. Thus, the first sensor 94 is able to output a detection value of each of the one or more detection elements, which indicates the amount of the odor-causing substance contained in air that has passed through the filter 34.

The second sensor 96 detects the amount of the odor-causing substance contained in air blown from the second fan 38 by using each of one or more incorporated detection elements. Thus, the second sensor 96 is able to output a detection value of each of the one or more detection elements, which indicates the amount of the odor-causing substance contained in air that has not passed through the filter 34.

(Effects of Embodiment)

The sensing system 10 according to the present embodiment has been described. Such a sensing system 10 according to the present embodiment leads to the following effect, for example.

The sensing system 10 according to the present embodiment is capable of determining an odor (the type of the odor and the intensity of the odor, for example) from the seat 32 (the seating part, the backrest, or the headrest, for example) being a target object as an odor source. In particular, the sensing system 10 determines an odor based on the difference between: the detection value of each of the one or more detection elements, which indicates the amount of the odor-causing substance contained in air having passed through the filter 34; and the detection value of each of the one or more detection elements, which indicates the amount of the odor-causing substance contained in air having not passed through the filter 34. Thus, the sensing system 10 is able to remove error components, such as noise occurring caused by adsorption of substances other than the causing substance to the adsorption film, and the like, and the offset of the sensor apparatus 30, for example. Thus, the sensing system 10 is able to detect the odor with high accuracy.

The sensing system 10 according to the present embodiment is able to install the sensor apparatus 30 close to the target object and thus determine the odor of the target object with high accuracy. In addition, the sensing system 10 performs measurement at a timing when there is no occupant, so that it is possible to determine an odor of the target object itself, from which an odor of an occupant has been excluded.

The sensing system 10 according to the present embodiment estimates the time at which a given odor occurs (the time at which the given type odor reaches a given intensity, for example), so that the user can clean the target object at an appropriate timing. Therefore, the sensing system 10 according to the present embodiment is able to reduce the burden of cleaning by the user and avoid a situation that dirt accumulates in the target object and the dirt is difficult to be removed.

The sensing system 10 according to the present embodiment measures an odor at a timing when an occupant enters the vehicle 18 and can thereby determine the odor of the occupant. The sensing system 10 is provided with the sensor apparatus 30 in a space where the occupant of the vehicle 18 can be identified, so that it is possible to determine the odor of the occupant while specifying the individual. Thus, the sensing system 10 may use the detected odor for health care information or the like of the individual.

(Hardware Configuration of Information Processing Apparatus 20)

Figure 12:
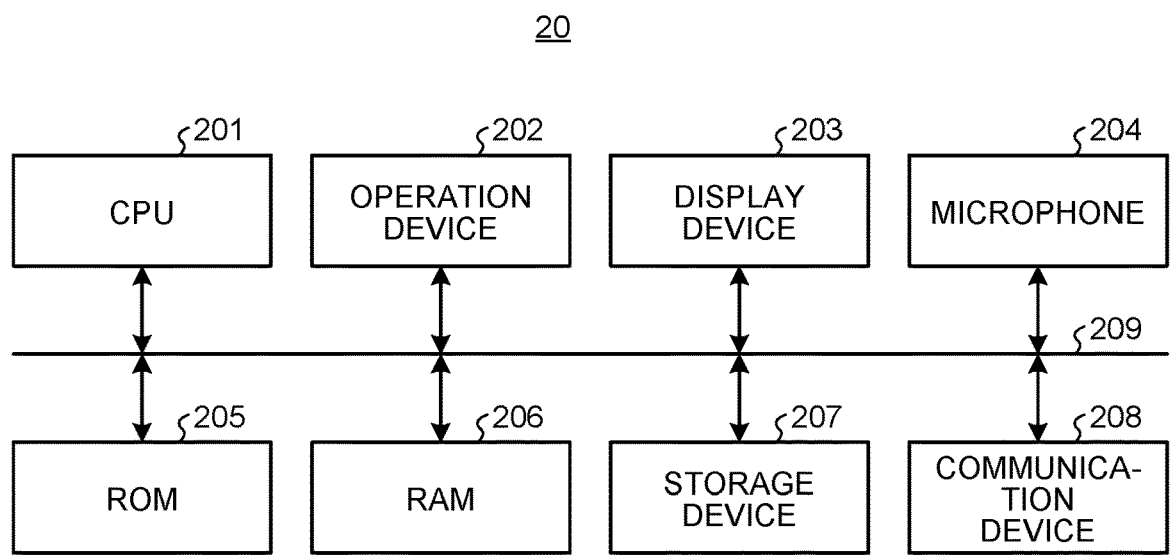
FIG. 12 is a diagram illustrating a hardware configuration of the information processing apparatus.

FIG. 12 is a diagram illustrating a hardware configuration of the information processing apparatus 20. The information processing apparatus 20 is implemented by, for example, a hardware configuration similar to that of a general computer. The information processing apparatus 20 includes a central processing unit (CPU) 201, an operation device 202, a display device 203, a microphone 204, a read only memory (ROM) 205, a random access memory (RAM) 206, a storage device 207, a communication device 208, and a bus 209. The units are connected with each other over the bus 209.

The CPU 201 executes various kinds of processing through cooperation with various kinds of computer programs stored in the ROM 205 or the storage device 207 in advance with a given area of the RAM 206 as workspace to comprehensively control operation of the units included in the information processing apparatus 20. The CPU 201 operates the operation device 202, the display device 203, the microphone 204, and the communication device 208 through cooperation with computer programs stored in the ROM 205 or the storage device 207 in advance.

The operation device 202 is an input device, such as a touch panel, a mouse, or a keyboard. The operation device 202 receives information as an instruction signal, which has been input through an operation made by the user, and outputs the instruction signal to the CPU 201.

The display device 203 is a display unit such as a liquid crystal display (LCD). The display device 203 displays various kinds of information based on display signals from the CPU 201. The display device 203 displays the type of odors, the intensity of odors, and an estimated time, for example.

The microphone 204 is a device for receiving input of voice signals. When voice signals recorded in advance or voice signals input from the communication device 208 are recognized, the information processing apparatus 20 does not necessarily include the microphone 204.

The ROM 205 stores computer programs, various kinds of setting information, and the like for use in control of the information processing apparatus 20 in a non-rewritable manner. The RAM 206 is a volatile storage medium such as a synchronous dynamic random-access memory (SDRAM). The RAM 206 functions as the workspace of the CPU 201.

The storage device 207 is a rewritable recording apparatus such as a semiconductor storage medium such as a flash memory or a magnetically or optically recordable recording medium. The storage device 207 stores the computer programs for use in control of the information processing apparatus 20. The storage device 207 functions as the pattern storage unit 78 and the log storage unit 84.

The communication device 208 transmits and receives data to and from the sensor apparatus 30. The communication device 208 may transmit and receive data to and from a server or the like over a network.

A computer program executed by the information processing apparatus 20 of the present embodiment is stored in a computer connected to a network such as the Internet and is provided by being downloaded over the network, for example. The computer program executed by the information processing apparatus 20 of the present embodiment may be recorded on a portable recording medium or the like in advance and be provided.

The computer program executed by the information processing apparatus 20 of the present embodiment has a module configuration including a first acquisition module, a second acquisition module, a difference calculation module, a determination module, an output module, and an estimation module. The CPU 201 (a processor) reads such a computer program from a storage medium or the like and loads the modules onto the RAM 206 (a main storage). The CPU 201 (the processor) then executes such a computer program to function as the first acquisition unit 72, the second acquisition unit 74, the difference calculation unit 76, the determination unit 80, the output unit 82, and the estimation unit 86. Part or the whole of the first acquisition unit 72, the second acquisition unit 74, the difference calculation unit 76, the determination unit 80, the output unit 82, and the estimation unit 86 may be configured by hardware.

The embodiments of the present invention have been described; these embodiments have been presented by way of example and do not intend to limit the scope of the invention. Various modifications can be made to the embodiments.

EXPLANATIONS OF LETTERS OR NUMERALS 10 sensing system
18 vehicle
20 information processing apparatus
30 sensor apparatus
32 seat
34 filter
36 first fan
38 second fan
40 sensor unit
48 communication unit
50 controller
52 battery
58 support
60 gas detection element
62 drive detection circuit
68 wall
72 first acquisition unit
74 second acquisition unit
76 difference calculation unit
78 pattern storage unit
80 determination unit
82 output unit
84 log storage unit
86 estimation unit
94 first sensor
96 second sensor

The invention claimed is:
1. A sensing system comprising:
a sensor apparatus including
  a filter configured to remove an odor-causing substance contained in air, and
  a sensor unit including one or more detection elements configured to detect an amount of the odor-causing substance contained in air; and
an information processing apparatus including
  a difference calculation unit configured to calculate a difference between
    a detection value of each of the one or more detection elements, the detection value indicating an amount of the odor-causing substance contained in air that has passed through the filter, and
    a detection value of each of the one or more detection elements, the detection value indicating an amount of the odor-causing substance contained in air that has not passed through the filter, and
  a determination unit configured to determine an odor of air based on the calculated difference,
wherein:
the information processing apparatus further includes a pattern storage unit configured to store one or more standard patterns in association with each of a plurality of types of odors,
the standard patterns each represent a detection value indicating the amount of the odor-causing substance contained in air of a corresponding odor of each of the one or more detection elements, and
the determination unit determines a type of the odor of air by performing matching between a difference pattern and the standard patterns, the difference pattern representing the difference between the detection value of each of the one or more detection elements, which indicates the amount of the odor-causing substance contained in air that has passed through the filter and the detection value of each of the one or more detection elements, which indicates the amount of the odor-causing substance contained in air that has not passed through the filter.

2. The sensing system according to claim 1, wherein the information processing apparatus further includes an estimation unit configured to estimate the difference pattern at a first time that is after the acquisition time, based on the difference pattern and an acquisition time of the detection value of the one or more detection elements serving as a base of the difference pattern, and determine an odor of air at the first time.

3. The sensing system according to claim 1, wherein the sensor apparatus further includes:

a first fan configured to cause air to pass through the filter and configured to supply the air to the sensor unit; and a second fan configured to cause air not to pass through the filter and configured to supply the air to the sensor unit.

4. The sensing system according to claim 2, wherein the information processing apparatus further includes an estimation unit configured to estimate the difference pattern at a first time that is after the acquisition time, based on the difference pattern and an acquisition time of the detection value of the one or more detection elements serving as a base of the difference pattern, and determine an odor of air at the first time.

5. The sensing system according to claim 3, wherein the sensor apparatus further includes a controller configured to switch between a first mode and a second mode, the first mode being a mode to cause the first fan to operate and cause the second fan to stop, the second mode being a mode to cause the first fan to stop and cause the second fan to operate, and the difference calculation unit calculates a difference between a detection value of each of the one or more detection elements in the first mode and a detection value of each of the one or more detection elements in the second mode.

6. The sensing system according to claim 3, wherein the information processing apparatus further includes an estimation unit configured to estimate the difference pattern at a first time that is after the acquisition time, based on the difference pattern and an acquisition time of the detection value of the one or more detection elements serving as a base of the difference pattern, and determine an odor of air at the first time.

* * * * *